United States Patent [19]

Hoffa

[11] 4,350,157
[45] Sep. 21, 1982

[54] ATRAUMATIC BLOOD ACCESS DEVICE VALVE

[75] Inventor: Jack Hoffa, Brea, Calif.

[73] Assignee: Bentley Laboratories, Irvine, Calif.

[21] Appl. No.: 156,259

[22] Filed: Jun. 3, 1980

[51] Int. Cl.³ .............................................. A61M 5/00
[52] U.S. Cl. .............................. 128/214 R; 128/1 R
[58] Field of Search .......... 128/213 A, 213 R, 214 R, 128/1 R, 274, 348, 350 R; 3/1

[56] References Cited

U.S. PATENT DOCUMENTS

| | | | |
|---|---|---|---|
| 4,015,601 | 4/1977 | Bokros et al. ................. | 128/214 R |
| 4,092,983 | 6/1978 | Slivenko ........................ | 128/214 R |
| 4,108,173 | 8/1978 | Slivenko et al. ............... | 128/214 R |
| 4,108,174 | 8/1978 | Slivenko ........................ | 128/214 R |
| 4,164,221 | 8/1979 | Bentley et al. ................. | 128/274 |

*Primary Examiner*—Kyle L. Howell
*Assistant Examiner*—T. J. Wallen
*Attorney, Agent, or Firm*—Lyon & Lyon

[57] ABSTRACT

A valving mechanism and method for use of such mechanism within a blood passageway of a blood access device. The valving mechanism includes a reciprocal plugging means which seals the blood passageway when the plugging means is in the closed position and which provides a blood channel for transfering blood therethrough only when said plugging means is reciprocated into its open valving mechanism position and means for reciprocating said plugging means between the closed and open valving mechanism positions.

5 Claims, 9 Drawing Figures

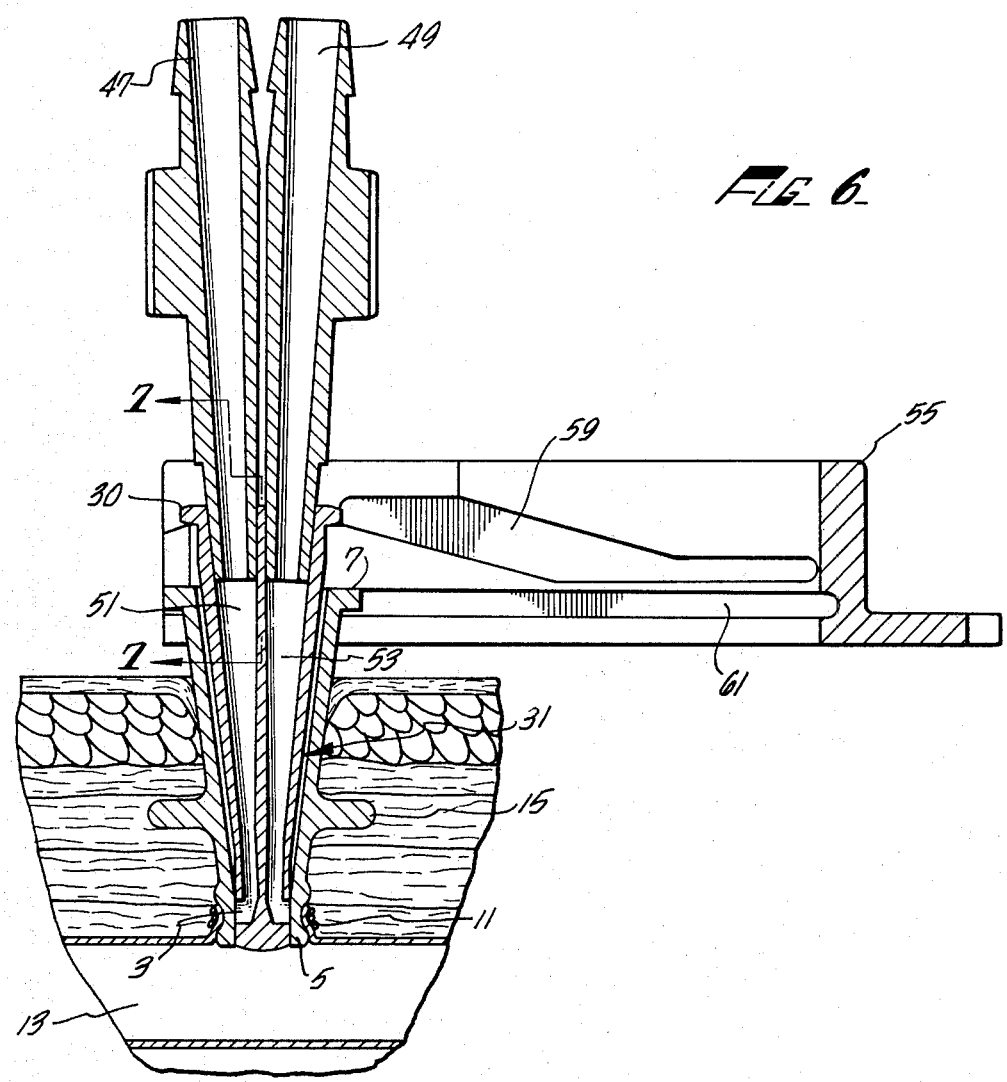
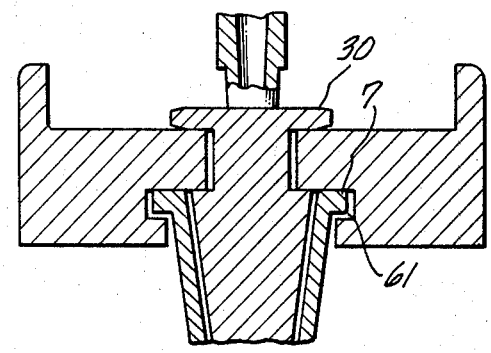

ATRAUMATIC BLOOD ACCESS DEVICE VALVE

BACKGROUND OF THE INVENTION

The present invention relates to a blood access device and its method of implantation.

There are a number of situations in which it is necessary to provide for fluid communication with the vascular system. For example, patients suffering from kidney failure require the dialysis of their blood by means external from the body. Blood containing toxic substances, such as urea, uric acid, creatine, phosphorus and calcium, must be removed from the blood system, treated and then returned to the patient. Patients requiring such blood dialysis require treatment at least two or three times per week. Patients suffering from hypoalimentation require a device for providing access to the body's vascular system on at least a daily basis.

One prior method of producing fluid communication with the vascular system involved the insertion of a needle into an artery from which blood to be treated was taken and the insertion of a needle into a patient's vein for blood return. Such a method proved unsatisfactory due to the difficulty in providing for the healing of the artery upon removal of the needle and the trauma produced by the repeated needle insertions. Such shortcomings led to the development of external and, later, internal shunts.

An external shunt involves the insertion of tubes, such as those made of Teflon, into an artery and an adjacent vein in a limb and providing an external communication or shunt between the tubes, which extend from the body of the patient. The shunt between the tube is required in order to provide flow through the tubes during that period of time that access is not required for blood treatment. Were such circulating blood flow not provided, a blood clot or thrombus could form as would be the case if the tubes were simply capped creating a static blood volume when the tubes were not in use. Dialysis, for example, is accomplished by connecting the arterial and venous tubing to a suitable dialysis unit. However, such a configuration traumatizes the skin adjacent the Teflon tubes and a path is provided through the skin for infection to enter the patient's body. Furthermore, even with external shunts, blood clots sometimes form with the tubes and create a health hazard to the patient.

The disadvantages of external shunts led to the development of the internal shunt. An internal shunt is performed by joining, within a body, openings between an artery and an adjacent vein. The pressure in the artery being substantially greater than that in the vein causes the vein to become distended, forming a fistula. One or two needles were then inserted into the fistula in order to achieve communication with the patient's vascular system. The patient suffers major discomfort and pain each time the needles are inserted into the fistula. Moreover, the continuous intrusion into the fistula causes it to become layered with scar tissue which ultimately prevents further intrusion, thus requiring the formation of another shunt.

Both the internal and external shunts increase the loading on the patient'heart due to the joining of the artery to a vein having a lower pressure, thereby lowering the artery's pressure, and requiring the heart to attempt to regain the original arterial blood pressure. Further, in many cases, the reduced circulation in the distal portion of the limb wherein the shunt is effected impairs the adequate removal of waste products from the muscles and other tissues resulting in weakness of the limb.

An object of the present invention is to provide an atraumatic valve for a blood access device. Other objects and advantages of this invention will become apparent upon a reading of the entire specification, including the drawings and claims.

DESCRIPTION OF THE DRAWINGS

FIGS. 6 and 8 are side views of the invention;

FIG. 7 is a cross-sectional view taken about 7—7 of FIG. 6; and

SUMMARY OF THE INVENTION

The present invention provides for a valve and its method of use in a blood access device which has been permanently implanted through a patient's skin in order to provide access to the patient's vascular system while enabling full circulation throughout the vascular system as no external or internal shunt is required. The device and method of operation may also be utilized for patients which have had an internal shunt operation. After a blood access device has been implanted within a patient's body providing access to a blood vessel of the patient's vascular system, the present invention provides for the atraumatic opening and closing of a valve within the blood access device allowing for blood treatment without trauma to the patient's blood or body tissues surrounding the blood access device. More particularly, this invention relates to a valving mechanism and method of use within a blood passageway of a blood access device. The valving mechanism includes a reciprocal plugging means which seals the blood passageway when the plugging means is in the closed position and which provides a blood channel for transferring blood therethrough only when said plugging means is reciprocated into its open valving mechanism position and means for reciprocating said plugging means between the closed and open valving mechanism positions.

BACKGROUND OF PREFERRED EMBODIMENTS

Figure 1:
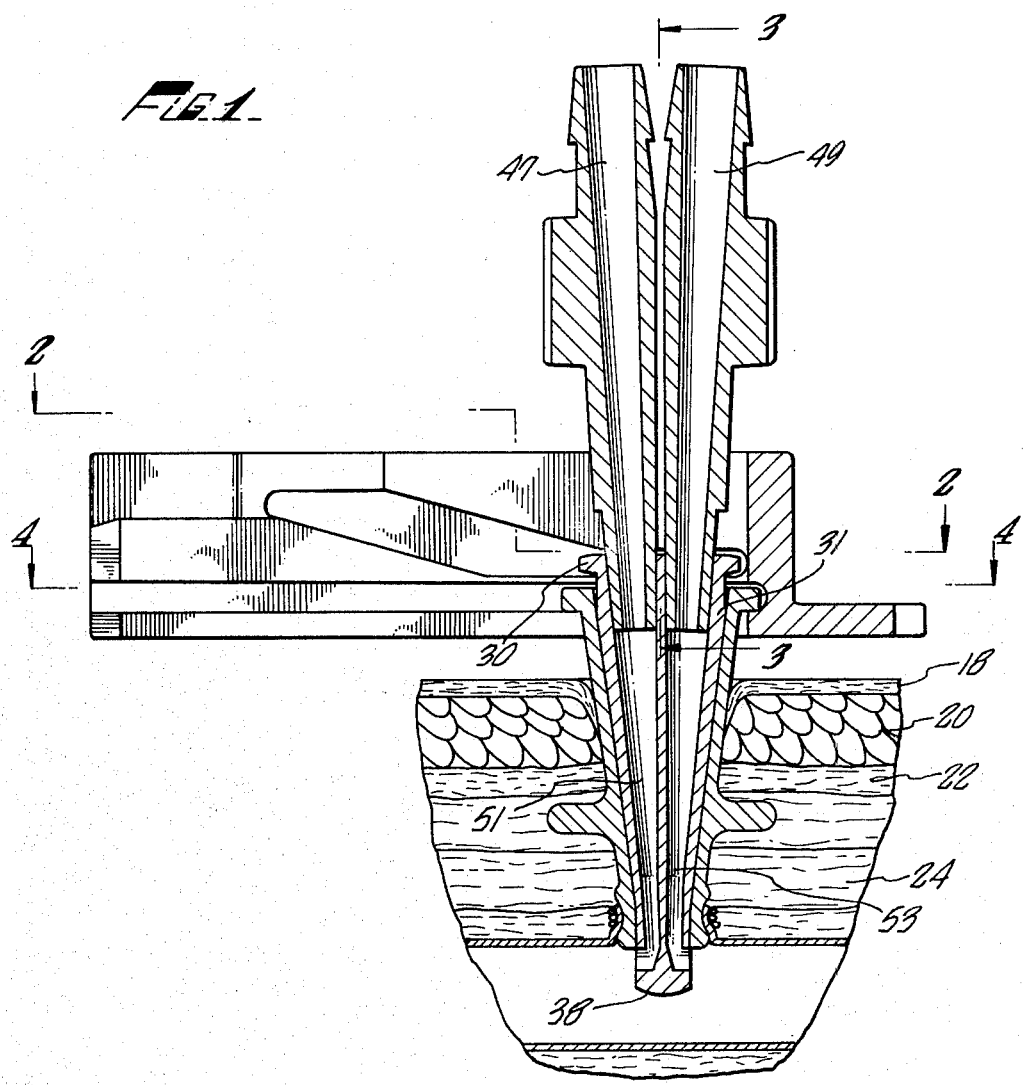
FIG. 1 is a side view of the invention in partial cross-section.
Figure 2:
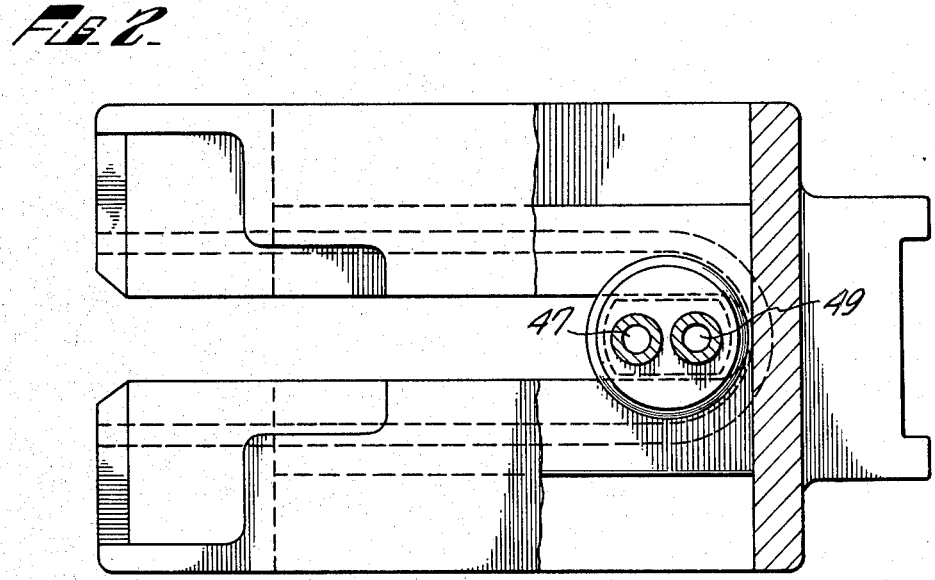
FIG. 2 is a cross-sectional view taken about 2—2 of FIG. 1.
Figure 3:
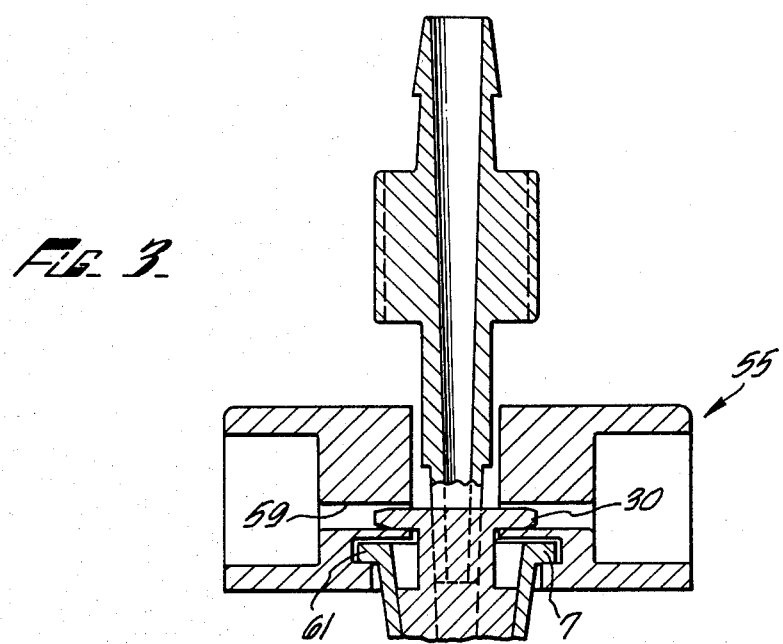
FIG. 3 is a cross-sectional view taken about 3—3 of FIG. 1.

Referring now to FIG. 1, the blood access device 1 within which the atraumatic valving mechanism of this invention operates, will be discussed. The blood access device 1 includes an external rim or lip 7, an anchor flange 14 and a flange means 5. The flange means 5 is secured through an aperature in a blood vessel 13 and secured thereto by means of suitable surgical suture fiber 11. In one embodiment, vascular grafting material such as Dacron which may be impregnated with collagen is provided at the juncture between the flange means 5 of the blood access device 1 and the blood vessel 13 in order to provide structural support for tissue ingrowth and allow the blood vessel 13 and the body tissues to be securely anchored to the blood access device 1. FIG. 1 illustrates a patient's, skin 18, fat 20, fascia 22 and muscle 24 within which the blood access device 1 has been anchored. The plugging means 31 is shown positioned within a passageway 3 provided in the blood access device 1, the plugging means 31 being adapted to prevent blood flow therethrough as illustrated in FIG. 6 where the valving mechanism of the invention is shown in the closed position. The passageway 3 of the blood access device 1 is preferably tapered, the taper having an untapered portion along its tapered length as shown as vertical ring 38 in order to provide an improved seal between the plugging means 31 and the passageway 3.

Figure 8:
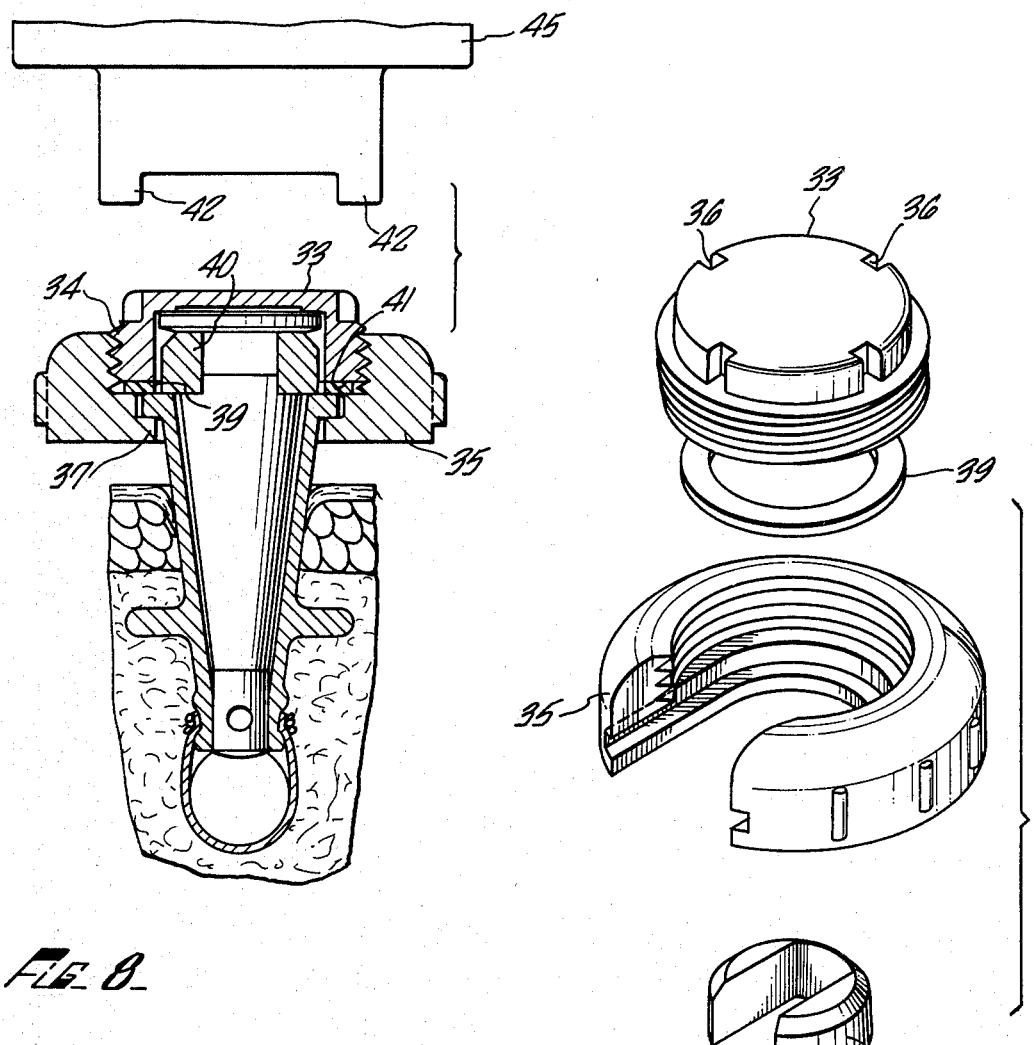
Figure 9:
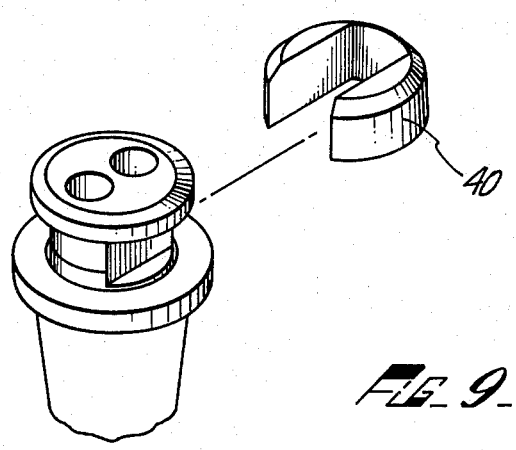
FIG. 9 is an assembly of the structure of the invention shown in FIG. 8.

As illustrated in FIG. 8, the plugging means 31 is preferably restrained within the passageway 3 of the blood access device 1 by means of a cap means 33 and an internally threaded retaining ring 35 which engages external threads 34 of the cap means 33. The cap means 33 is preferably provided with notches 36 which may be engaged for threading and engaging the corresponding threads of the cap means 33 and the threaded retaining ring 35 in order to secure the plugging means 31 in a sealed position as illustrated in FIG. 8. The threaded retaining ring 35 is preferably provided with an inwardly extending lip 36 which engages the rim or lip 7 of the blood access device as the threads of the cap means 33 and the threaded retaining ring 35 are engaged. A stop ring 40 is positioned between the inner portion of the rim 7 of the blood access device 1 and the underside of the rim 30 of plugging means 31 in order to ensure that the plugging means 31 does not move from its secured closed position as shown in FIG. 8. A gasket means 39 may be positioned about the outer portion of the rim 7 of the blood access device 1. A shoulder 41 of the cap means 33 bears upon such gasket means 39 and in turn upon the outer portion of the rim 7 of the blood access device 1. As may be clearly seen in FIG. 8, such a configuration allows for the securing of the cap means 33 to the blood access device 1 in a vice-like configuration as the inwardly engaging lip 37 of the threaded retaining ring 35 bears upwardly against the lower portion of the blood access device rim 3 while the cap means 33 is urged downwardly by the threading engagement of the cap means 33 and the ring 35 against the upper portion of the rim 7 of the blood access device 1. The cap means threads may be tightened by insertion of member 42 of an actuator means 45, later discussed, the legs 42 engaging the notches 36 of the cap means 33.

Referring now to FIGS. 6 and 7, the valving mechanism is shown in the closed position as was true in FIG. 8, however, the cap means 33, threaded retaining ring 35, gasket means 39 and stop ring 40 have been removed. An inlet and outlet chamber 47 and 49 respectively, have been inserted within corresponding blood channel inlet 51 and blood channel outlet 53 within the plugging means 31.

Figure 4:
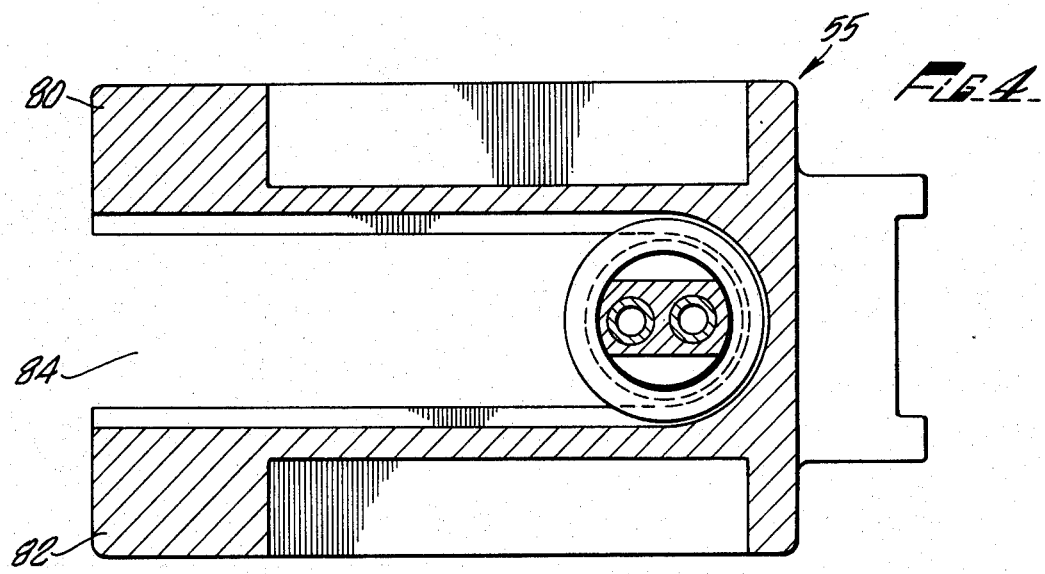
FIG. 4 is a cross-sectional view taken about 4—4 of FIG. 1.
Figure 5:
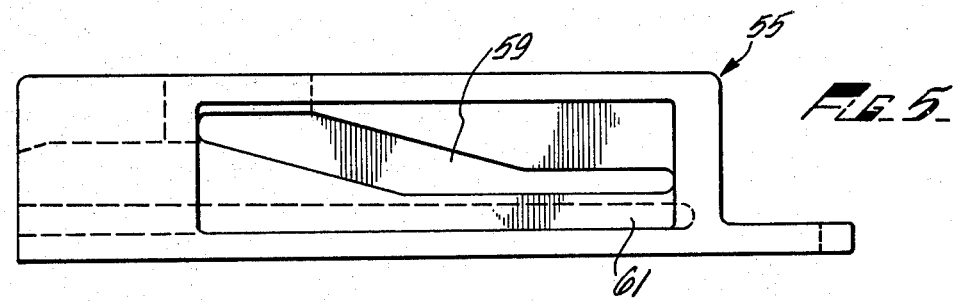
FIG. 5 is a side view of the structure of the invention shown in FIG. 4.

Actuating means 55, shown in greater detail in FIGS. 4 and 5, has been inserted between the rim 7 of the blood access device 1 and the plugging means rim 30 in place of the stop ring 40 in order to maintain the plugging means in the closed valving mechanism position shown in FIG. 6. The actuator means includes a cam surface 59 for engagement between the blood access device rim 7 and the plugging means rim 30. As the actuator means 55 is moved laterally from the position shown in FIG. 6 to the figure shown in FIG. 1, the plugging means 31 together with inlet chamber 47 and outlet chamber 49 are urged into the interior of the blood vessel 13 and the blood channel inlet 51 and blood channel outlet 53 of the plugging means 31 are exposed to the blood flowing therethrough. Such lateral movement of the actuator means 55 urges such movement by the plugging means 31 due to configuration cam surface 59 of the actuator means 55. This cam surface is illustrated in detail in FIGS. 1, 5 and 6. The rim 7 of the blood access device 1 is constrained within a slot 61 of the actuator means 55 while the movement of the plugging means rim 30 and the corresponding relationship between the plugging means 31 and the blood access device 1 is determined by the tapered configuration of member 59 of actuator means 55

As shown in FIG. 4, actuator means 55 includes two opposed leg members 80 and 82 and an aperature there between 84 so as to allow actuating means 55 to slidably engage rim 7 within slot 61 and plugging means rim 30 within cam surface 59.

Accordingly, the present invention allows for communication with the interior of a blood vessel which may be interrupted by actuation of the activator means 55 such that the communication with the blood vessel 13 to the body exterior is utilized when necessary for blood treatment.

While the preferred embodiments in the application of this invention have been shown and described, it would be apparent to those skilled in the art that modifications thereto may be made without departing from the inventive concepts described herein. The invention is, therefore, to be limited only by the scope of the claims appended hereto.

What is claimed is:

1. An atraumatic valving mechanism for operation within a blood access device, said blood access device adapted to connect a blood vessel within a body to the body exterior, said valving mechanism comprising:

a reciprocal plugging means for sealing said blood access device when said plugging means assumes a closed valving mechanism position, and further including first and second blood channels for transferring blood through said plugging means from said blood vessel through said first blood channel and to said blood vessel through said second blood channel only when said plugging means is reciprocated into a open valving mechanism position wherein said plugging means is extended from said blood access device for extending said first and second blood channels into said blood vessel; and actuator means for reciprocating said plugging means between said closed valving mechanism position and said open valving mechanism position.

2. The atraumatic valving mechanism claimed in claim 1 wherein said plugging means is generally correspondingly tapered along its length but includes a ring of substantially constant diameter at its end forming a substantially blood tight seal when said plugging means assumes said valving mechanism closed position.

3. An atraumatic valving mechanism for operation within a blood access device having an external rim, said blood access device adapted to connect a blood vessel within a body to the body exterior, said valving mechanism comprising:

a reciprocal plugging means for sealing said blood access device when said plugging means assumes a closed valving mechanism position, said plugging means including a plugging means external rim and an interior blood channel for transferring blood therethrough only when said plugging means is reciprocated into an open valving mechanism position wherein said plugging means is extended from said blood access device for extending said first and second blood channels; and actuator means for slidably engaging said blood access device external rim and said plugging means external rim and for varying the position of said plugging means external rim relative to said blood access device external rim, for reciprocating said plugging means between said closed valving mechanism position and said open valving mechanism position.

4. An atraumatic valving mechanism for operation within a blood passageway of a blood access device having an external rim, said blood passageway adapted to connect a blood vessel within a body to the body exterior, said valving mechanism comprising:

a reciprocal plugging means for sealing said blood passageway when said plugging means assumes a closed valving mechanism position, said plugging means including a plugging means external rim and an interior blood channel for transferring blood therethrough only when said plugging means is reciprocated into an open valving mechanism position; and actuator means for slidably engaging said blood access device external rim and said plugging means external rim and for varying the position of said plugging means external rim relative to said blood access device external rim, for reciprocating said plugging means between said closed valving mechanism position and said open valving mechanism position wherein said actuator means is further defined as including an aperture for sliding said actuator means about said blood access device rim and plugging means external rim bounded by two opposed leg members, each of said leg members including a slot for engaging said blood access device rim and a cam surface of increasing taper for insertion, and varying separation, between said blood access device external rim and said plugging device external rim.

5. An atraumatic valving mechanism for operation within a blood access device having an external rim, said blood access device adapted to connect a blood vessel within a body to the body exterior, said valving mechanism comprising:

a reciprocal plugging means for sealing said blood access device when said plugging means assumes a closed valving mechanism position, said plugging means including a plugging means external rim and an interior blood channel for transferring blood therethrough only when said plugging means is reciprocated into an open valving mechanism position; and actuator means for reciprocating said plugging means between said closed valving mechanism position and said open valving mechanism position wherein said actuator means is further defined as including an aperture for sliding said actuator means about said blood access device rim and plugging means external rim bounded by two opposed leg members, each of said leg members including a slot for engaging said blood access device rim and a cam surface of increasing taper for insertion, and varying separation between said blood access device external rim and said plugging device external rim.

* * * * *